(12) United States Patent
Holmström et al.

(10) Patent No.: US 8,682,428 B2
(45) Date of Patent: Mar. 25, 2014

(54) IMPLANTABLE MEDICAL DEVICE WITH THERAPY CONTROL

(75) Inventors: Nils Holmström, Järfälla (SE); Kjell Noren, Solna (SE)

(73) Assignee: St. Jude Medical AB, Jarfalla (SE)

( * ) Notice: Subject to any disclaimer, the term of this patent is extended or adjusted under 35 U.S.C. 154(b) by 1125 days.

(21) Appl. No.: 12/094,534

(22) PCT Filed: Nov. 30, 2005

(86) PCT No.: PCT/SE2005/001807
§ 371 (c)(1),
(2), (4) Date: May 21, 2008

(87) PCT Pub. No.: WO2007/064260
PCT Pub. Date: Jun. 7, 2007

(65) Prior Publication Data
US 2008/0294213 A1 Nov. 27, 2008

(51) Int. Cl.
*A61N 1/00* (2006.01)

(52) U.S. Cl.
USPC ........ 607/9; 607/17; 607/18; 607/19; 607/24; 607/25; 607/27; 600/508; 600/510; 600/513; 600/528

(58) Field of Classification Search
USPC .......... 607/17, 18, 9, 24, 25, 27, 19; 600/508, 600/510, 513, 514, 528
See application file for complete search history.

(56) References Cited

U.S. PATENT DOCUMENTS

| | | | |
|---|---|---|---|
| 5,554,177 A | 9/1996 | Kieval et al. | |
| 5,700,283 A | 12/1997 | Salo | |
| 6,643,548 B1 | 11/2003 | Mai et al. | |
| 6,792,308 B2 | 9/2004 | Corbucci | |
| 6,885,889 B2 * | 4/2005 | Chinchoy | 607/9 |
| 7,130,689 B1 * | 10/2006 | Turcott | 607/27 |
| 2002/0151938 A1 | 10/2002 | Corbucci | |
| 2004/0106960 A1 | 6/2004 | Siejko et al. | |
| 2004/0106961 A1 | 6/2004 | Siejko et al. | |
| 2004/0127792 A1 * | 7/2004 | Siejko et al. | 600/439 |
| 2004/0186524 A1 | 9/2004 | Chinchoy | |
| 2004/0230249 A1 | 11/2004 | Haefner | |
| 2005/0102001 A1 | 5/2005 | Maile et al. | |
| 2005/0102002 A1 | 5/2005 | Salo et al. | |
| 2006/0020294 A1 | 1/2006 | Brockway et al. | |

* cited by examiner

*Primary Examiner* — Michael Kahelin
*Assistant Examiner* — Mallika D Fairchild (57) ABSTRACT

A method for operating an implantable medical device to obtain substantially synchronized closure of the mitral and tricuspid valves based on sensed heart sounds includes sensing an acoustic energy; producing signals indicative of heart sounds of the heart of the patient over predetermined periods of a cardiac cycle during successive cardiac cycles; calculating a pulse width of such a signal; and iteratively controlling a delivery of the ventricular pacing pulses based on calculated pulse widths of successive heart sound signals to identify an RV interval or VV interval that causes a substantially synchronized closure of the mitral and tricuspid valve. A medical device for optimizing an RV interval or VV interval based on sensed heart sounds implements such a method and a computer readable medium encoded with instructions causes a computer to perform such a method.

27 Claims, 11 Drawing Sheets

IMPLANTABLE MEDICAL DEVICE WITH THERAPY CONTROL

BACKGROUND OF THE INVENTION

1. Field of the Invention

The present invention generally relates to implantable medical devices, such as cardiac pacemakers and implantable cardioverter/defibrillators, and in particular to a method, a medical device, a computer program product and a computer readable medium for operating an implantable medical device to obtain substantially synchronized closure of the mitral and tricuspid valves based on sensed heart sounds.

2. Description of the Prior Art

Auscultation is an important diagnostic method for obtaining information of the heart sounds, which is well established as diagnostic information of the cardiac function. The sounds are often described as S1-S4. During the working cycle of the heart mechanical vibrations are produced in the heart muscle and the major blood vessels. Acceleration and retardation of tissue cause the vibrations when kinetic energy is transformed to sound energy, e.g. at valve closing. Vibrations can also arise from turbulent blood flow, e.g. at stenosis and regurgitation. These vibrations may be listened to using a stethoscope or registered electronically using phonocardiography, i.e. graphical registration of the heart sounds by means of a heart microphone placed on the skin of the patient's thorax. Auscultation using a stethoscope is, to a large extent, built on practical experience and long practice since the technique is based on the doctor's interpretations of the hearing impressions of heart sounds. When applying phonocardiography, as mentioned above, a heart microphone is placed on the skin of the patient's thorax. In other words, it may be cumbersome and time-consuming to obtain knowledge of the heart sounds and the mechanical energy during the heart cycle using these manual or partly manual methods and, in addition, the obtained knowledge of the heart sounds may be inexact due to the fact that the knowledge is, at least to some extent, subjective.

The first tone S1 coincides with closure of the Mitral and Tricuspid valves at the beginning of systole. Under certain circumstances, the first tone S1 can be split into two components. An abnormally loud S1 may be found in conditions associated with increased cardiac output (e.g. fever, exercise, hyperthyroidism, and anemia), tachycardia and left ventricular hypertrophy. A loud S1 is also characteristically heard with mitral stenosis and when the P-R interval of the EKG is short. An abnormally soft S1 may be heard with mitral regurgitation, heart failure and first degree A-V block (prolonged P-R interval). A broad or split S1 is frequently heard along the left lower sternal border. It is a rather normal finding, but a prominent widely split S1 may be associated with right bundle branch block (RBBB). Beat-to-beat variation in the loudness of S1 may occur in atrial fibrillation and third degree A-V block.

The second heart sound S2 coincides with closure of the aortic and pulmonary valves at the end of systole. S2 is normally split into two components (aortic and pulmonary valves at the end of systole) during inspiration. Splitting of S2 in expiration is abnormal. An abnormally loud S2 is commonly associated with systemic and pulmonary hypertension. A soft S2 may be heard in the later stages of aortic or pulmonary stenosis. Reversed S2 splitting (S2 split in expiration—single sound in inspiration) may be heard in some cases of aortic stenosis but is also common in left bundle branch block (LBBB). Wide (persistent) S2 splitting (S2 split during both inspiration and expiration) is associated with bundle branch block, for example, right bundle branch block, pulmonary stenosis, pulmonary hypertension, or atrial septal defect.

The third heart sound S3 coincides with rapid ventricular filling in early diastole. The third heart sound S3 may be found normally in children and adolescents. It is considered abnormal over the age of 40 and is associated with conditions in which the ventricular contractile function is depressed (e.g. CHF and cardiomyopathy). It also occurs in those conditions associated with volume overloading and dilation of the ventricles during diastole (e.g. mitral/tricuspid regurgitation or ventricular septal defect). That S3 may be heard in the absence of heart disease in conditions associated with increased cardiac output (e.g. fever, anemia, and hyperthyroidism).

The fourth heart sound S4 coincides with atrial contraction in late diastole. S4 is associated with conditions where the ventricles have lost their compliance and have become "stiff". S4 may be heard during acute myocardial infarction. It is commonly heard in conditions associated with hypertrophy of the ventricles (e.g. systemic or pulmonary hypertension, aortic or pulmonary stenosis, and some cases of cardiomyopathy). The fourth heart sound S4 may also be heard in patients suffering from CHF.

Thus, the systolic and diastolic heart functions are reflected in the heart sound. The heart sounds and their relation carry information of the workload and status of the heart. For example, as discussed above, patients with a wide QRS complex due to e.g. right bundle branch block (RBBB), left bundle branch block (LBBB), or A-V block are associated with a widened or split first heart sound S1. Knowledge of the heart sounds and the mechanical energy during the heart cycle can be used both for diagnosis/monitoring and controlling therapy of such patients. In case of right bundle branch block (RBBB) or A-V block, the patient is normally stimulated with RV or VV pacing intervals selected on basis of echocardiographic studies performed to determine the settings resulting in the best hemodynamic response. After evaluation of hemodynamic effect of varying combinations of pacing intervals, a physician must manually select and program the desired parameters and assume that the optimal setting of the device remain unchanged until a subsequent reoptimization visit. Therefore, automated systems for selecting pacing intervals would be useful in presence of cardiac conditions such as right bundle branch block (RBBB), left bundle branch block (LBBB) or A-V block.

The known technique presents a number of automated systems for controlling/optimizing stimulation therapy as, for example, U.S. Pat. No. 6,792,308, which discloses an implantable medical device, such as a cardiac pacemaker, adapted to sense first and second heart sounds and to optimize the A-V interval using the detected first and second heart sounds. In WO 2004/078257, a method and apparatus for monitoring left ventricular cardiac contractility and for optimizing a cardiac therapy based on left ventricular lateral wall acceleration are disclosed.

However, the prior art does not disclose a method for controlling the stimulation therapy in patients suffering from a wide QRS complex caused by, for example, right bundle branch block (RBBB), left bundle branch block (LBBB) or A-V block on an automated basis using detected or monitored heart sounds.

SUMMARY OF THE INVENTION

Thus, an object of the present invention is to provide a method and medical device for controlling the stimulation therapy in patients suffering from a wide QRS complex caused by, for example, right bundle branch block (RBBB), left bundle branch block (LBBB) or A-V block on an automated basis using detected or monitored heart sounds.

As used herein, the terms "AV interval" or "AV delay" refers to, in dual chamber devices, the length of time (e.g. in ms) between an atrial sensed or atrial paced event and the delivery of a ventricular output pulse. An AV delay or interval may be terminated if an intrinsic ventricular event is sensed before the AV delay times out. Hence, AV interval can be used as a common descriptor for AV, AR, PR, or PV intervals.

According to an aspect of the present invention, there is provided an implantable medical device including a pulse generator adapted to produce cardiac stimulating pacing pulses. The device is connectable to at least one lead comprising electrodes for delivering the pulses to cardiac tissue in at least one ventricle of a heart of a patient. The implantable medical device has a signal processing circuit adapted to extract a signal corresponding to a first heart sound (S1) from a sensed signal, this signal being received from an acoustic sensor adapted to sense an acoustic energy and to produce signals indicative of heart sounds of the heart of the patient over predetermined periods of a cardiac cycle during successive cardiac cycles, and to calculate a pulse width of the extracted signal. The device has a memory adapted to store the calculated pulse width and/or the extracted signal corresponding to the first heart sound and a controller adapted to initiate an optimization procedure. Delivery of the ventricular pacing pulses is controlled iteratively based on calculated pulse widths of successive heart sound signals to identify an RV interval or VV interval that causes a substantially synchronized closure of the mitral and tricuspid valves.

According to a second aspect of the present invention, there is provided a method for operating an implantable medical device to obtain substantially synchronized closure of the mitral and tricuspid valves, the device including a pulse generator adapted to produce cardiac stimulating pacing pulses and is connectable to at least one lead comprising electrodes for delivering the pulses to cardiac tissue in at least one ventricle of a heart of a patient. The method includes the steps of: sensing an acoustic energy; producing signals indicative of heart sounds of the heart of the patient over predetermined periods of a cardiac cycle during successive cardiac cycles; extracting a signal corresponding to a first heart sound (S1) from a sensed signal; calculating a pulse width of an extracted signal; storing the calculated pulse width and/or the extracted signal corresponding to the first heart sound; and initiating an optimization procedure. The optimization procedure includes iteratively controlling a delivery of the ventricular pacing pulses based on calculated pulse widths of successive heart sound signals to identify an RV interval or VV interval that causes a substantially synchronized closure of the mitral and tricuspid valves.

According to a third aspect of the present invention, there is provided a computer program product, which when executed on a computer, performs steps in accordance with the first aspect of the present invention.

According to a further aspect of the present invention, there is provided a computer readable medium comprising instructions for bringing a computer to perform a method according to the first aspect of the present invention.

Thus, the invention is based on the idea of controlling the stimulation therapy in patients suffering from a wide QRS complex caused by, for example, right bundle branch block (RBBB), left bundle branch block (LBBB) or A-V block on an automated basis using detected or monitored heart sounds by using the pulse widths of successively signals corresponding to first heart sound signals. In particular, pulse widths of signals corresponding to first heart sounds are calculated and a delivery of ventricular pacing pulses is iteratively controlled based on measured or calculated pulse widths of successive heart sound signals to identify an RV interval or VV interval that causes a substantially synchronized closure of the mitral and tricuspid valve. This invention provides several advantages. For example, one advantage is that the optimization procedure for identifying an RV or VV delay that causes a substantially synchronized closure of the mitral and tricuspid valve can be performed on an automated basis. Another advantage is that the optimization can adapt to changing conditions of a heart of patient in a fast and reliable way since intrinsic information of the heart, i.e. the heart sounds, is used as input to the optimization procedure. The optimization is also accurate due to the facts that the systolic and diastolic heart functions are reflected in the heart sound, and that the hearts sounds and their relations thus carry information of the workload and status of the heart.

According to an embodiment of the present invention, the ventricular pacing pulses are controlled such that the pulse widths of the heart sound signals are within a predetermined range of pulse widths. This predetermined range may be programmable, which entails that the range can be adjusted for different patients or adjusted in response to changing conditions of a patient and thus the RV interval or VV interval can be optimized with a high degree of accuracy. Alternatively, the ventricular pacing pulses can be controlled such that the pulse widths of the heart sound signals are minimized. Thereby, an RV interval or VV interval that synchronizes a closure of the mitral and tricuspid valve can be obtained in an accurate and automated way.

In an embodiment of the present invention, each pulse width is calculated as a mean value over a predetermined number of successive pulse widths of heart sound signals. Thereby, a more reliable and accurate pulse width can be obtained. Alternatively, a weighted average value of a predetermined number of successive pulse widths of heart sound signals can be used. In still another embodiment, a moving average of a predetermined number of successive pulse widths of heart sound signals is utilized.

According to an embodiment of the present invention, frequency components of a sensed signal outside a predetermined frequency range is filtered off to reduce noise content of the received signal, an absolute value of the filtered signal is determined; and a pulse width is calculated using the filtered signal. Furthermore, the calculation of the pulse width can be based on a part of the filtered signal above a predetermined amplitude threshold, which threshold may be programmable. This also reduces the noise content of the signal. Alternatively, signal corresponding to a first heart sound (S1) is extracted from a sensed signal by selecting a part of the sensed signal above a predetermined amplitude threshold, which threshold may be programmable. The pulse width is calculated based on the selected part of the signal.

In another embodiment of the present invention, an activity level of the patient is sensed and it is checked whether the sensed activity level is below a predetermined activity level. If it is determined the sensed activity level is below the predetermined activity level or activity level range, the optimization procedure is initiated. By performing the optimization at stable conditions, e.g. correlating the optimization procedure with a predetermined activity level, the accuracy and reliability of the procedure can be further enhanced. This predetermined activity level can, for example, be set such that the optimization is performed at rest. That is, in this case an RV or VV delay that is optimal for situations when the patient is at rest can be obtained.

According to yet another embodiment of the present invention, an activity level of the patient is sensed and it is checked whether the sensed activity level is below a predetermined first activity level (or within a first range) or within a second activity level range between a second activity level and a third activity level, wherein second activity level can be equal to or higher than the first activity level or equal to or higher than an upper limit of the first range. If the sensed activity level is found to be below the predetermined first activity level, an optimization procedure is initiated to identify a first RV interval or VV interval that synchronizes the mitral and tricuspid valve closure below the first activity level, and if the sensed activity level is found to be within the activity level range, an optimization procedure is initiated to identify a second RV interval or VV interval that synchronizes the mitral and tricuspid valve closure in the activity level range. Thus, the optimization can be performed at two activity levels, and the RV or VV interval can be optimized, for example, at rest and at an elevated activity level (e.g. at exercise), respectively. By knowing the optimal RV or VV delay at two activity levels, it is possible to extrapolate the data to obtain a rate adaptive RV or VV delay based on the time for AV valve closure.

According to an alternative embodiment, a heart rate of the patient is sensed and it is determined whether the sensed heart rate is within a predetermined heart rate interval. If it is determined that the sensed heart rate is within the predetermined heart rate interval, an optimization procedure is initiated. By performing the optimization at stable conditions, e.g. correlating the optimization procedure with a predetermined heart rate level, the accuracy and reliability of the optimization procedure can be further improved.

In a further embodiment of the present invention, the optimization procedure is performed at unchanged pacing rate and at a predetermined AV delay range. By performing the optimization at stable conditions, e.g. correlating the optimization procedure with a predetermined heart rate level, the accuracy and reliability of the optimization procedure can be enhanced even further.

According to another embodiment, a body position of the patient is detected and it is determined whether the patient is in at least one predetermined specific body position. If it is determined that the patient is in the predetermined position, an optimization procedure is initiated. By performing the optimization at stable conditions, e.g. correlating the optimization procedure with a predetermined position, the accuracy and reliability of the optimization procedure can be improved.

In alternative embodiments, the optimization can be synchronized with anyone, some, or all of the following: heart rate, activity level, AV delay, pacing rate, or position of patient.

In yet another embodiment of the present invention, the optimization includes iteratively adjusting interventricular pacing timing parameters for pacing electrodes based on the calculated pulse widths of successive heart sound signals. Furthermore, the extracted signal corresponding to the first heart sound resulting from a pacing pulse can be stored together with the pacing timing parameters of the electrodes for the pacing pulse and, for each applied pacing pulse, a calculated pulse width of a present heart sound signal is compared with pulse widths of preceding heart sound signals resulting from preceding pacing pulses to determine an adjustment of the interventricular pacing timing parameters for the electrodes.

In embodiments, the acoustic sensor is arranged in a lead connectable to the device and is located e.g. in the right ventricle of the heart of the patient or on the epicardial surface in a coronary vein. Other locations is also possible, for example, the sensor may be placed in the right atrium.

According to embodiments, the acoustic sensor is an accelerometer, a pressure sensor or a microphone.

In an alternative embodiment, the sensor is arranged within a housing of the implantable device.

As will be apparent to those skilled in the art, the methods of the present invention, as well as preferred embodiments thereof, are suitable to realize as a computer program or a computer readable medium.

DESCRIPTION OF THE PREFERRED EMBODIMENTS

Figure 1:
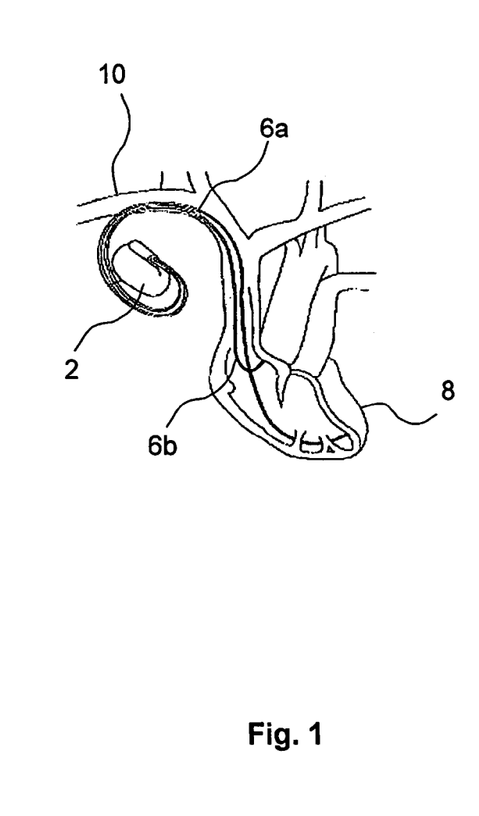
FIG. 1 is schematic diagram showing a medical device implanted in a patient in which device the present invention can be implemented.

With reference to FIG. 1, there is shown a schematic diagram of a medical device implanted in a patient in which device the present invention can be implemented. As seen, this embodiment of the present invention is shown in the context of a pacemaker 2 implanted in a patient (not shown). The pacemaker 2 comprises a housing being hermetically sealed and biologically inert. Normally, the housing is conductive and may, thus, serve as an electrode. The pacemaker 2 is connectable to one or more pacemaker leads, where only two are shown in FIG. 1 namely a ventricular lead 6a and an atrial lead 6b. The leads 6a and 6b can be electrically coupled to the pacemaker 2 in a conventional manner. The leads 6a, 6b extend into the heart 8 via a vein 10 of the patient. One or more conductive electrodes for receiving electrical cardiac signals and/or for delivering electrical pacing to the heart 8 are arranged near the distal ends of the leads 6a, 6b. As the skilled man in the art realizes, the leads 6a, 6b may be implanted with its distal end located in either the atrium or ventricle of the heart 8, or in the coronary sinus or in the cardiac vein or in a coronary vein on the left ventricle, or they may be in form of epicardial leads attached directly at the epicardium.

Figure 2:
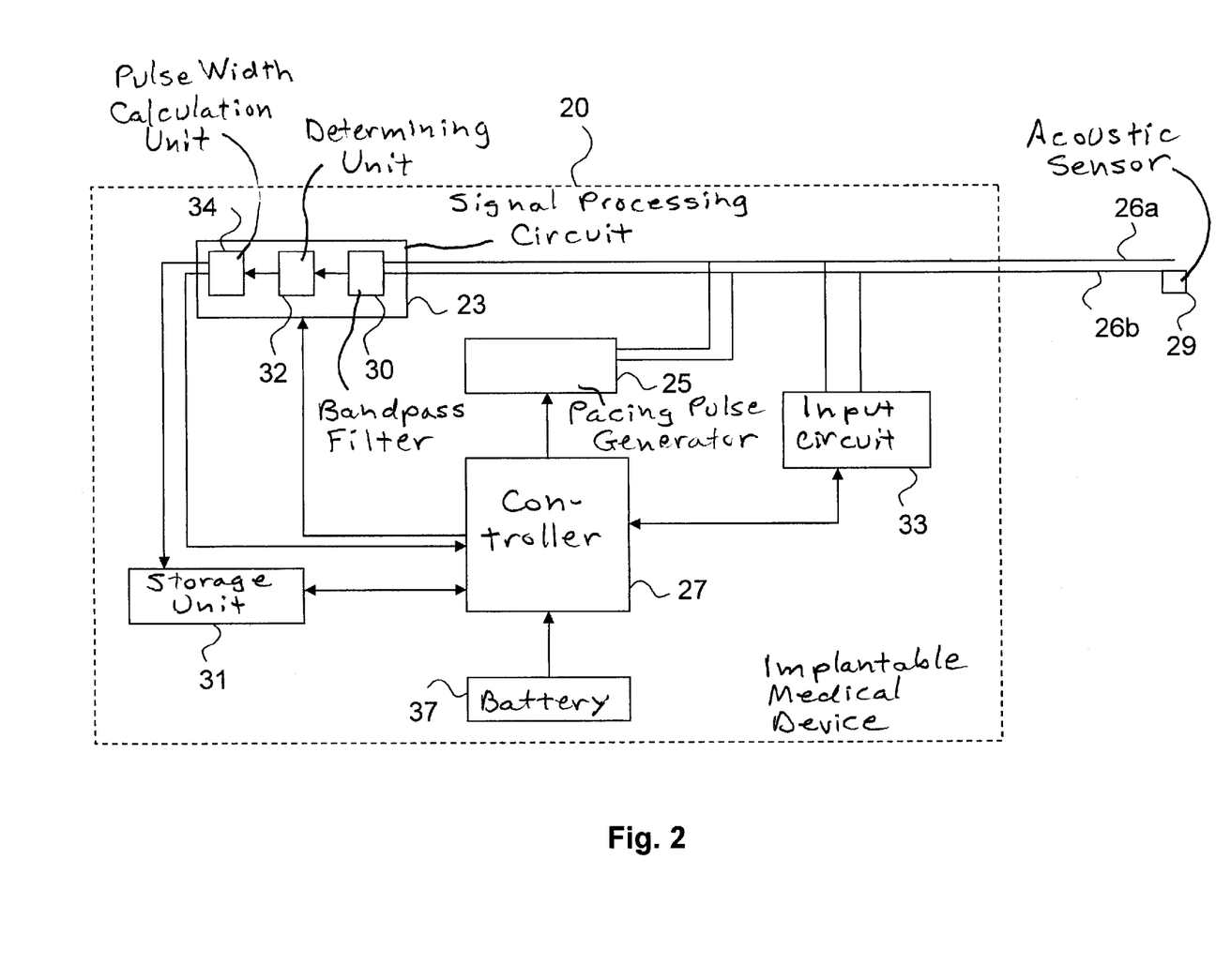
FIG. 2 is block diagram of the primary functional components of an embodiment of the medical device according to the present invention.

With reference now to FIG. 2, the configuration including the primary components of an embodiment of the present invention will be described. The illustrated embodiment includes an implantable medical device 20, such as the pacemaker shown in FIG. 1. Leads 26a and 26b, of the same type as the leads 6a and 6b shown in FIG. 1, are connectable to the device 20. The leads 26a, 26b may be unipolar or bipolar, and may include any of the passive or active fixation means known in the art for fixation of the lead to the cardiac tissue. As an example, the lead distal tip (not shown) may include a tined tip or a fixation helix. The leads 26a, 26b comprises one or more electrodes (as described with reference to FIG. 1), such as a tip electrode or a ring electrode, arranged to, inter alia, measure the impedance or transmit pacing pulses for causing depolarization of cardiac tissue adjacent to the electrode(-s) generated by a pacing pulse generator 25 under influence of a controller 27 including, inter alia, a microprocessor. The controller 27 controls, for example, pace pulse parameters such as output voltage and pulse duration.

Furthermore, an acoustic sensor 29 is arranged in or connected to one of the leads 26a, 26b. Alternatively, the acoustic sensor 29 is located within the housing of the device 20. In one embodiment, the acoustic sensor 29 is arranged in a lead located in a right ventricle of the heart, in coronary sinus or the great cardiac vein of the patient. The acoustic sensor 29 may, for example, be an accelerometer, a pressure sensor or a microphone. The acoustic sensor 29 is adapted to sense acoustic energy of the heart and to produce signals indicative of heart sounds of the heart of the patient. For example, the acoustic sensor 29 may sense the acoustic energy over predetermined periods of a cardiac cycle during successive cardiac cycles. In one embodiment of the present invention, a sensing session to obtain a signal indicative of a first heart sound (S1) is synchronized with a detected heart event, e.g. detection of an intrinsic or paced QRS-complex.

Furthermore, the implantable medical device 20 has a signal processing circuit 23 adapted to process the sensed signal to extract a signal corresponding to a first heart sound (S1) and to calculate a pulse width of the extracted signal. In one embodiment, the signal processing circuit 23 includes preprocessing circuits including at least one bandpass filter 30 adapted to filter off frequency components of the heart sound signal outside a predetermined frequency range, for example, 10-300 Hz, and a determining circuit 32 adapted to determine the absolute value of the bandpass filtered signal and to produce a resulting absolute value heart sound signal. Alternatively, a rectifier can be used to rectify the filtered signal. The signal processing circuit 23 also has a pulse width calculation unit 34 adapted to calculate a pulse width of the filtered signal. The pulse width calculation unit 34 will be described in detail hereinafter with reference to FIG. 6.

A storage unit 31 is connected to the controller 27. The storage unit 31 may include a random access memory (RAM) and/or a non-volatile memory such as a read-only memory (ROM). Detected signals from the patients heart are processed in an input circuit 33 and are forwarded to the controller 27 for use in logic timing determination in known manner, for example, a detected QRS-complex. The implantable medical device 20 is powered by a battery 37, which supplies electrical power to all electrical active components of the medical device 20. Data contained in the storage unit 31 can be transferred to a programmer (not shown) via a programmer interface (not shown) for use in analyzing system conditions, patient information, etc.

Figure 3:
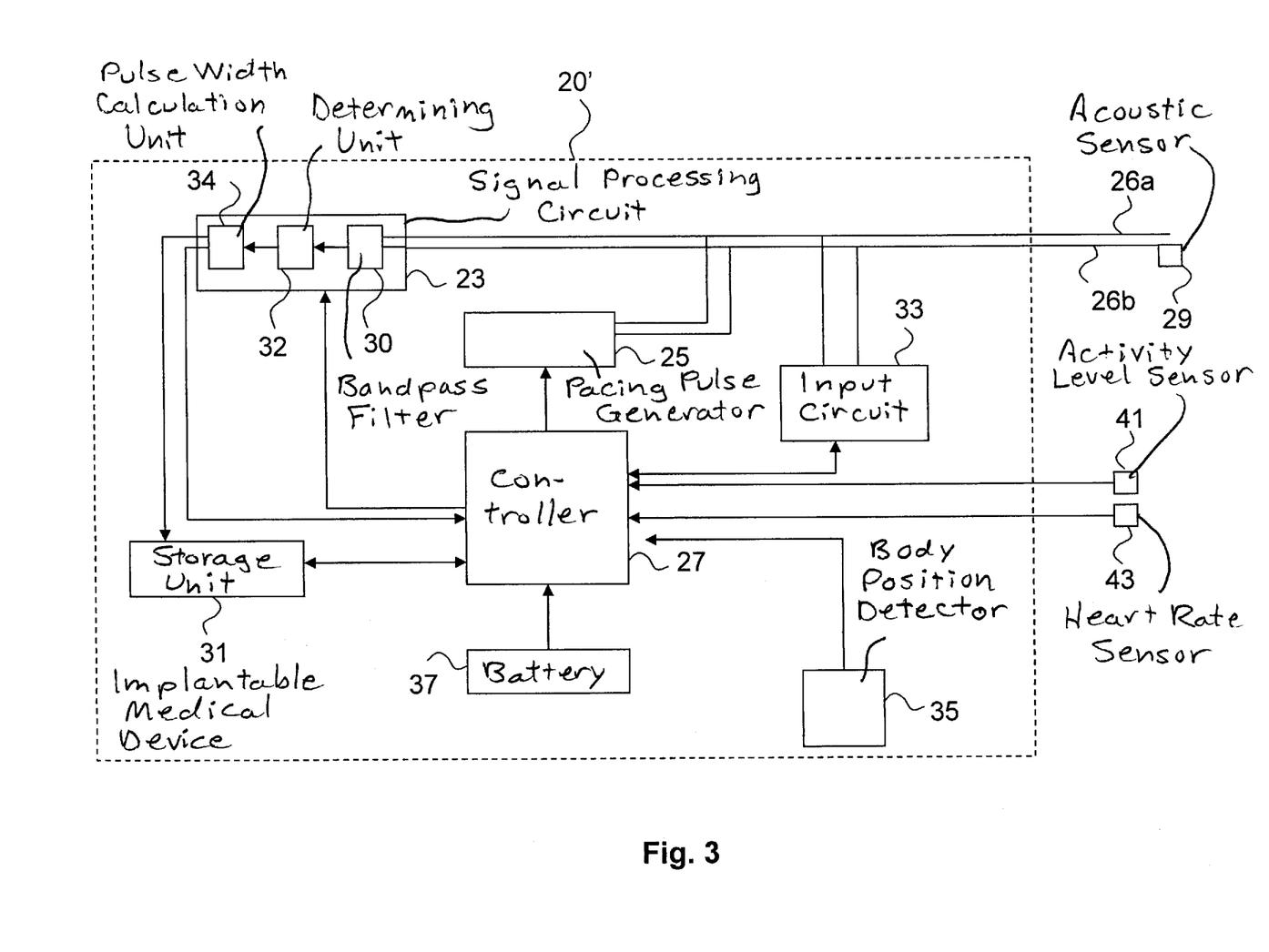
FIG. 3 is a block diagram of the primary functional components of another embodiment of the medical device according to the present invention.

With reference now to FIG. 3, another embodiment of the present invention will be described. Like parts in FIG. 2 and FIG. 3 are denote with the same reference numeral and the description thereof will be omitted since they have been described with reference to FIG. 2. The implantable medical device 20' may include activity level sensor 41 for sensing an activity level of the patient connected to the controller 27. The controller 27 may be adapted to determine whether a sensed activity level is below a predetermined activity level and to initiate an optimization procedure to identify an RV interval or VV interval that causes a substantially synchronized closure of the mitral and tricuspid valve if the sensed activity level is below the predetermined activity level. By performing the optimization at stable conditions, e.g. correlating the optimization procedure with a predetermined activity level, the accuracy and reliability of the procedure can be further enhanced. This predetermined activity level can, for example, be set such that the optimization is performed at rest.

In an alternative embodiment, the controller 27 is adapted to determine whether a sensed activity level is below a predetermined first activity level or within an activity level range between a second activity level and a third activity level, wherein the second activity level is equal to or higher than the first activity level. If the sensed activity level is determined to be below the predetermined first activity level, an optimization procedure to identify a first RV interval or VV interval that synchronizes the mitral and tricuspid valve closure below the first activity level is initiated. Moreover, if the sensed activity level is within the activity level range, an optimization procedure to identify a second RV interval or VV interval that synchronizes the mitral and tricuspid valve closure in the activity level range is initiated. Hence, the optimization can be performed at two activity levels, and the RV or VV interval can be optimized, for example, at rest and at an elevated activity level (e.g. at exercise), respectively. The controller 27 may be adapted to extrapolate the data, i.e. the optimal RV or VV delay at the two activity levels, to obtain a rate adaptive RV or VV delay based on the time for AV valve closure.

In addition, the implantable medical device 20' may include heart rate sensor 43 for sensing a heart rate of the patient connected to the controller 27. The controller 27 may be configured to determine whether a sensed heart rate is within a predetermined heart rate interval and to initiate an optimization procedure if the sensed heart rate is determined to be within the predetermined heart rate interval.

Moreover, the implantable medical device 20' may include a body position detector 35 that detects the body position of the patient. For example, the position detector 35 may detect a predetermined specific body position. In a one embodiment of the present invention, the body position detector 35 is a back-position sensor arranged to sense when the patient is lying on his or her back (or on his or her face). The body position detector 35 is connected to the controller 27.

Furthermore, the implantable medical device 20 may include a sensor for sensing signals related to the heart pumping activity of the patient (not shown) connected to the controller 27, which may be adapted to determine an AV interval of the patient. The controller 27 can be adapted to determined whether a sensed AV interval is within a predetermined AV interval range and to initiate the optimization procedure if the sensed AV interval is within the predetermined AV interval range. The memory unit 31 may be adapted to store an extracted signal corresponding to the first heart sound resulting from a pacing pulse together with the sensed AV interval.

As those skilled in the art will appreciate, only one, some of or all of the following features: the activity level sensor 41, the heart rate sensor 43, a breathing rate sensor, a blood temperature sensor, the position detector 35, or the means for sensing signals related to the heart pumping activity of the patient may be included in the medical device according to the present invention.

Figure 4:
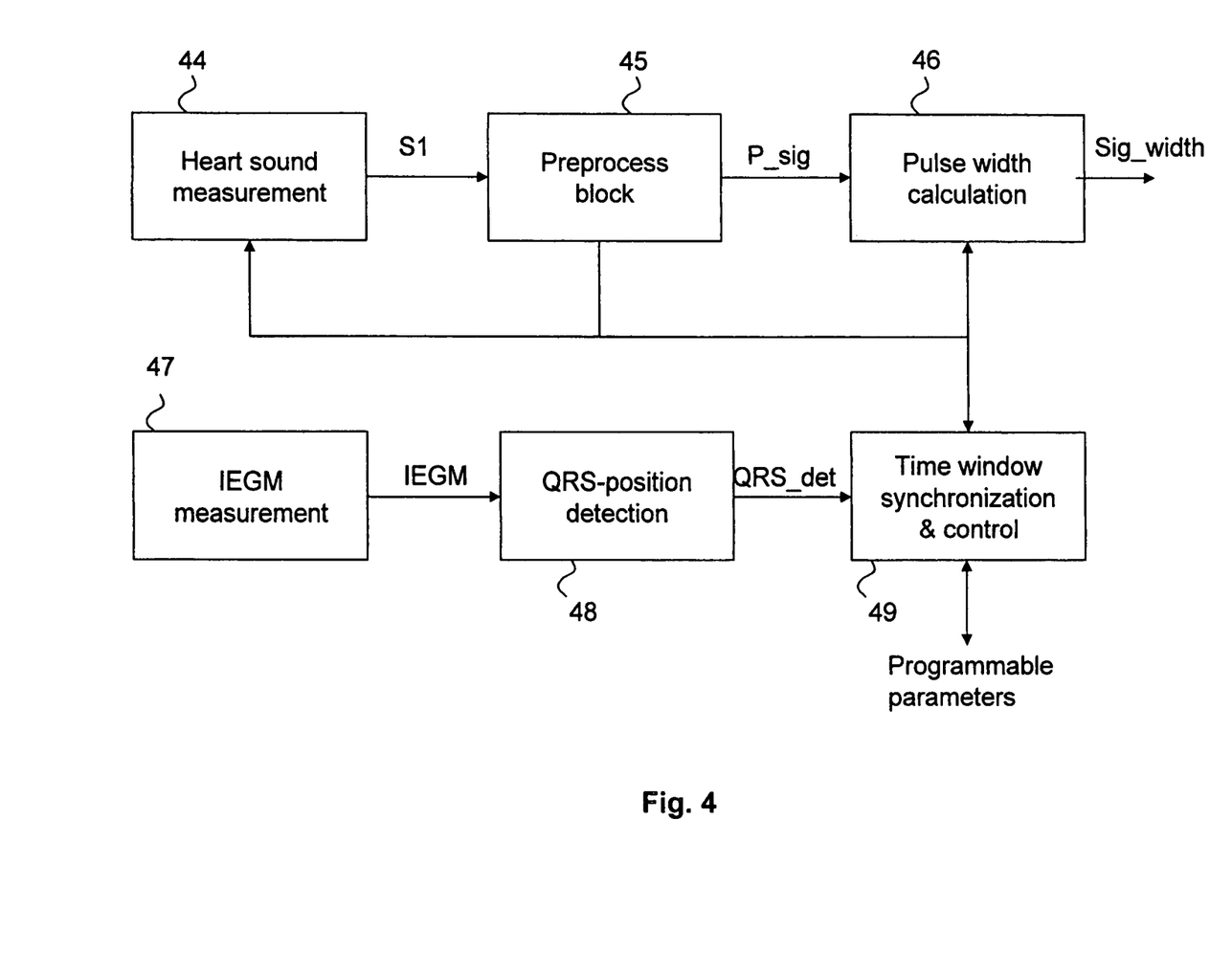
FIG. 4 is schematic block description of the main blocks of the signal processing and pulse width calculation according to one embodiment of the present invention.

With reference now to FIG. 4, the main functional blocks of the signal processing and the pulse width calculation according an embodiment of the present invention will be described. The sensing or measurement of the signals corresponding to the first heart sounds (S1) is performed in a heart sound measurement block 44. This measurement block 44 can, for example, be implemented by the acoustic sensor 29 described above with reference to FIG. 2. The sensed heart sound S1 is transferred to a pre-process block 45 where the sensed signal is processed to obtain a processed signal, P_sig, suitable for pulse width calculation. In one example, the pre-processing includes band-pass filtering and rectifying the input signal. The pre-processing block 45 can be implemented by the pre-processing circuits 30 and 32 described with reference to FIG. 2. Then, the pre-processed signal, P_sig, is fed to a pulse width calculation block 46 where the pulse width, Sig_width, of the pre-processed signal is calculated. This block may be implemented by the pulse width calculation circuit 34 described with reference to FIGS. 2 and 7. The measurement or sensing of the heart sounds is synchronized with heart events. In a IEGM measurement block 47, intracardiac signals are measured, and in a QRS-position detection block 48, intrinsic or paced heart events are detected. In this embodiment, the onset of a QRS-complex is detected. In a time window synchronization & control block 49, a received signal indicating the onset of a heart event, QRS_det, initiates a measurement time window during which a heart sound sensing session is performed. That is, at detection of the onset of a QRS-complex, the time window synchronization & control block 49 receives a QRS_det signal, which, in turn, triggers the start of a measurement time window and a first heart sound S1 can thus be cut out. This will be described in more detail hereinafter with reference to FIGS. 7-11. The block 47 and 48 can be realized by means of the leads 26a, 26b comprising electrodes connected to the input circuit 33 described above with respect to FIG. 2. The time window synchronization & control block 49 can be implemented in the controller 27. Parameters of the time window synchronization & control block 49 are programmable, for example, the length of the time window.

Figure 5:
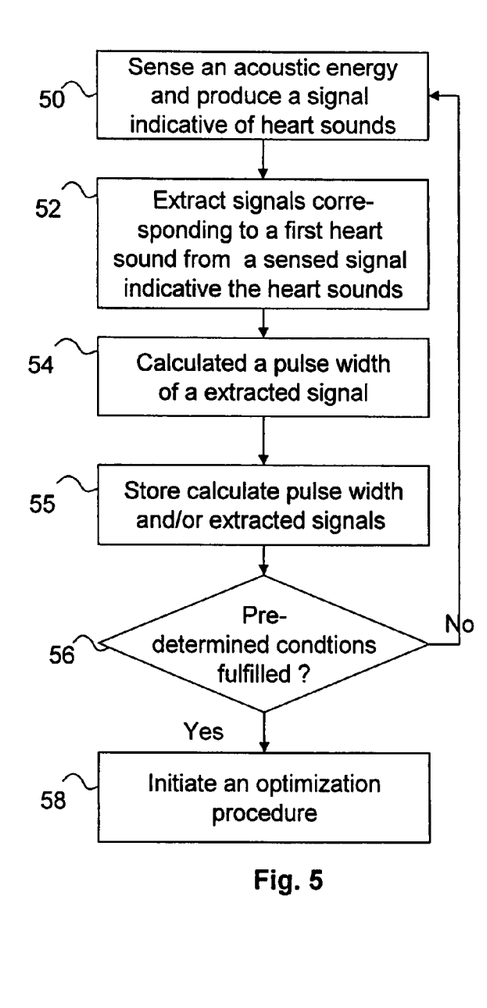
FIG. 5 is a flow chart of an embodiment of the method according to the present invention.
Figure 6:
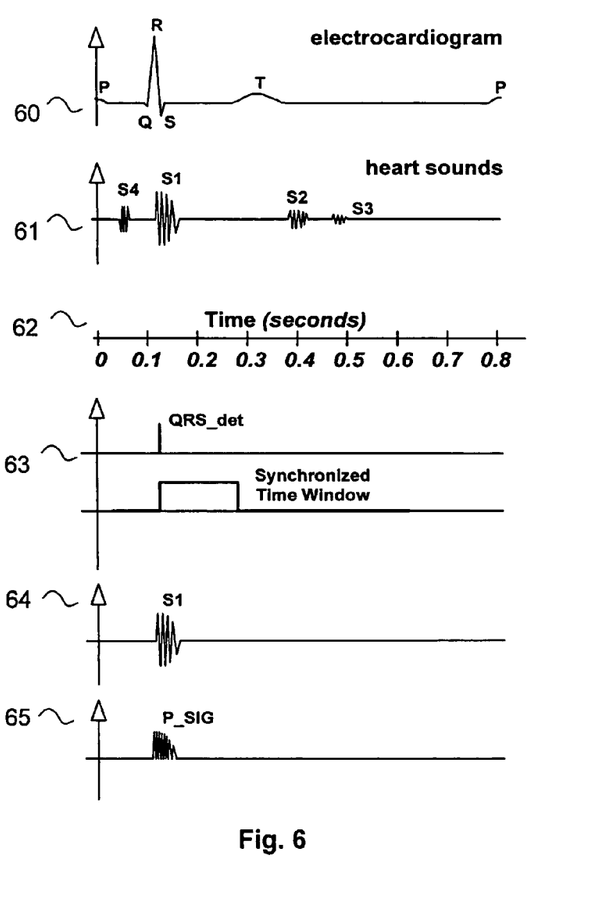
FIG. 6 shows a typical cardiac cycle, related heart sounds, and the resulting signals at a heart rate of 75 BPM.

Turning now to FIG. 5, a high-level description of the method according to the present invention will be given. First, at step 50, the acoustic sensor 29 senses an acoustic energy and produces signals indicative of heart sounds of the heart of the patient. In FIG. 6, a typical cardiac cycle, related heart sounds, and the resulting signals at a heart rate of 75 BPM are shown. A surface electrocardiogram and the related heart sounds S1, S2, S3, and S4 are indicated by 60 and 61, respectively, and a time axis is indicated by 62. In one embodiment, the acoustic sensor 29 is activated by the detection of a QRS-position, as indicated by 63, by a intrinsic detected event or a paced event indicated by 60. The acoustic sensor 29 senses the acoustic energy in the heart sound S1, indicated by 62, during a sensing session or predetermined time window indicated by 63. In this embodiment, the initiation of the sensing session is synchronized with the detection of the QRS-position. The length of the time window is programmable and a typical length is about 200 ms. Hence, the acoustic sensor 29 receives a triggering signal from the controller 27 upon detection of the QRS-position by the input circuit 33. The produced signal corresponding to the first heart sound S1 is indicated by 64. This may be performed during successive cardiac cycles under control of the controller 27, which thus produces a time series of successive heart sound signals. The produced signal or signals indicative of the first heart sounds are supplied to the signal processing circuit 23 where, at step 52, a signal corresponding to a first heart sound (S1) is extracted from a sensed signal by the pre-processing circuits 30, 32. Optionally, this step may include performing a filtering procedure in order to filter the sensed signal. In one embodiment, frequency components of the signal outside a predetermined frequency range is filtered off and the absolute value of the sensed signal is calculated. The resulting signal is indicated by 65 in FIG. 6. In another embodiment, the first heart sound signal is determined to be a part of the sensed signal having an amplitude above a predetermined amplitude level.

Thereafter, at step 54, a pulse width of the extracted signal, indicated by 65 in FIG. 6, corresponding to the first heart sound is calculated in the pulse width calculation block 34. Then, at step 55, the calculated pulse width and/or the extracted signal can be stored in the memory unit 31. If signals corresponding to the first heart sound is obtained for successive cardiac cycles, the signals and calculated pulse widths can be stored in the memory means 31 in consecutive time order. Subsequently, at step 58, an optimization procedure is initiated. Optionally, a check whether conditions, such as activity level of the patient or position of the patient, are suitable for performing an optimization procedure can be performed before the optimization procedure is initiated. That is, the optimization procedure is initiated only if certain predetermined conditions are fulfilled, for example, that a sensed activity level is within a predetermined activity level range. Thus, optionally, a optimization procedure condition check step 56 may be performed before the optimization procedure is initiated. If the predetermined condition (-s) is (are) fulfilled, the optimization step 58 is initiated. On the other hand, if the predetermined condition (-s) is (are) not fulfilled, the procedure returns to step 50.

The optimization procedure comprises the step of iteratively controlling a delivery of pacing pulses based on calculated pulse widths of successive heart sound signals to identify an RV interval or VV interval that causes a substantially synchronized closure of the mitral and tricuspid valve. In one embodiment, the delivered pacing pulses are iteratively controlled such that the pulse widths of the heart sound signals are within a predetermined range of pulse widths. In another embodiment, the delivered ventricular pacing pulses are iteratively controlled such that the pulse widths of the heart sound signals are minimized. This is based on the findings that patients with a wide QRS complex due to e.g. right bundle branch block (RBBB), left bundle branch block (LBBB), or A-V block are associated with a widened or split first heart sound S1. Therefore, by iteratively adjusting the delivered pacing pulses with respect to the pulse widths of successive first heart sounds is it possible to identify an RV interval or VV interval that causes a substantially synchronized closure of the mitral and tricuspid valves. The optimization may be performed according to the following. The controller 27 may be adapted to iteratively adjust pacing timing parameters of pacing electrodes based on calculated pulse widths of successive heart sound signals, i.e. for, each applied pacing pulse, compare a pulse width of a present heart sound signal with pulse widths of preceding heart sound signals resulting from preceding pacing pulses to determine an adjustment of the pacing timing parameters of the electrode or electrodes.

Figure 7:
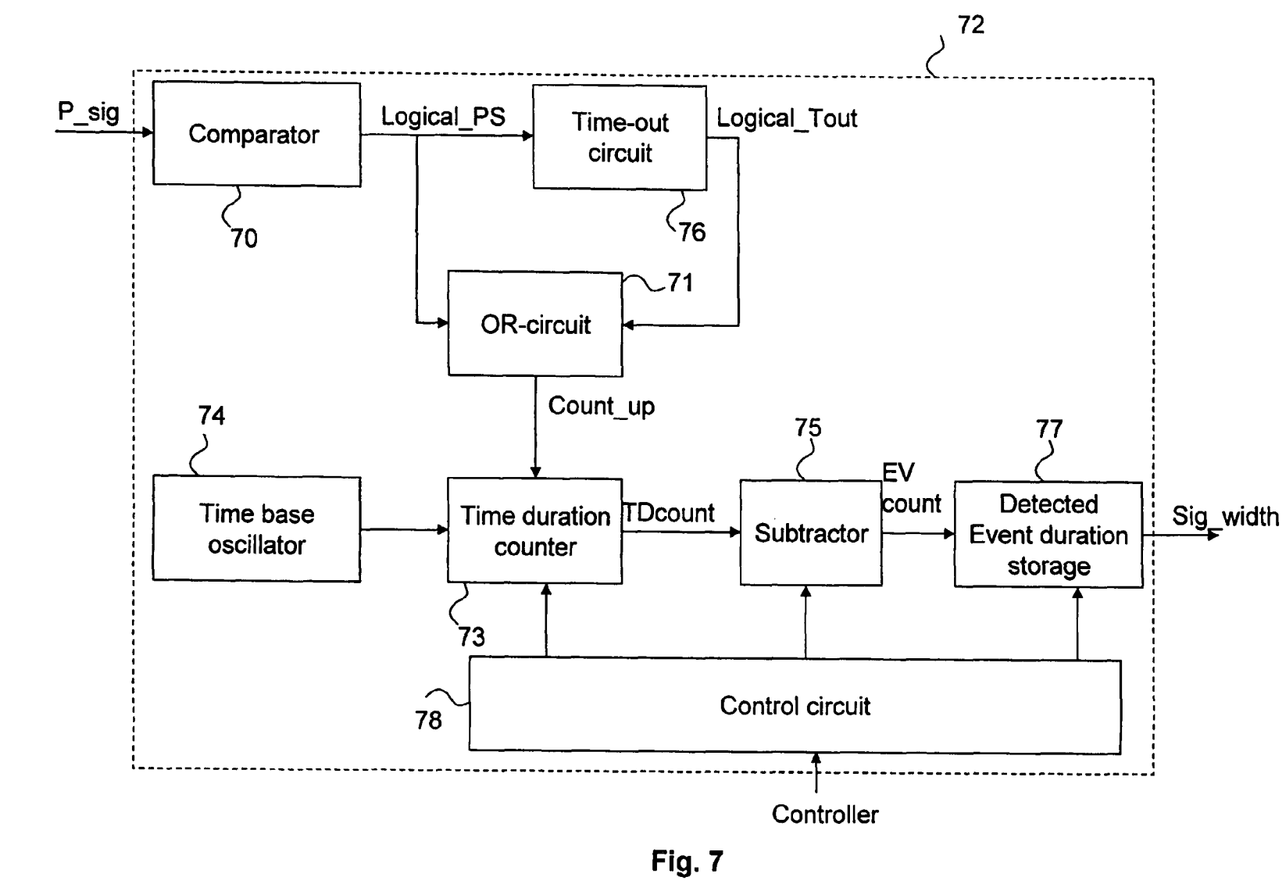
FIG. 7 is block diagram of functional components of an embodiment of the pulse width calculation block according to the present invention.

With reference now to FIG. 7, one embodiment of the pulse width calculation block will be described. As mentioned above, the extracted signal, P_sig, i.e. rectified signal or the absolute value of the filtered signal, is supplied to a pulse width calculation block from the pre-processing circuits. The pulse width calculation block 72 includes a comparator 70 adapted to convert the received signal, P_sig, to a logical signal, Logical_PS. In this embodiment, the comparator is an amplitude threshold comparator with hysteresis, where a logical 1 corresponds to a signal above the amplitude threshold and a logical 0 corresponds to a signal below the amplitude threshold, which threshold is programmable. Preferably, the amplitude level is sensed with a small hysteresis to decrease the influence of noise in the signal. The positive level is sensed slightly above the low level. The comparator 70 is connected to an OR-circuit 71 and a time-out circuit 76, which also is connected to the OR-circuit 71. The time-out circuit 76 is adapted to connect a fluctuating amplitude level of the incoming signal, P_sig, to the comparator 70 that results in alternating logical levels of the logical output signal, Logical_PS, from the comparator 70 to occur within the same duration of the first heart sound S1. The time-out period Tout can for instance be programmed to 30 ms. The OR-circuit 71 receives the output signal, Logical_PS, from the comparator 70 and the output signal, Logical_Tout, from the time-out circuit 76. The output signal, Logical_Tout, has a high level duration equal to the predetermined time out period Tout in seconds defined to accept splitted high level occurrences of, P_sig, to be in the same detected event. Each trailing edge of the comparator output signal, Logical_PS, restarts a new time-out period, Tout, of a predetermined time duration. The OR-circuit 71 is connected to a time duration counter 73, which, in turn, is connected to a time base oscillator 74 and a subtractor 75. The pulse width time of, P_sig, is measured by counting the periods of the time base oscillator 74 in the time duration counter 73. An NTcount period of the time base oscillator 74 can be set, in one example the NTcount period is set equal to the Tout period. The frequency of the oscillator 74 may, for example, be 1000 Hz, which gives a time resolution of 1 ms. The OR-circuit 71 supplies a Count_up signal, which is the sum of Logical_PS and, Logical_Tout, to the time duration counter 73. The time duration counter 73 sums the measured representative of pulse width of event duration and the Tout duration, the NTcount, and the output signal TDcount is supplied to the subtractor 75. An arithmetic subtraction is performed on the received TDcount signal in the subtractor 75 to obtain an EVcount signal (EVcount=TDcount−NTcount), which thus is the measured duration of the first heart sound S1. That is, a duration Sig_width (the measured duration of S1) is represented by EVcount. The calculated pulse width EVcount is stored in a detected event duration storage 77. The measured duration Sig_width can be stored, for example, in the memory unit 31 for use in an optimization procedure and may also be supplied directly to the controller 27 for use in the optimization procedure. A control circuit 78 controls, under influence of the controller 27, the time duration counter 73, the subtractor 75 and the detected event duration storage 77. The control circuit 78 resets the time duration counter 74 and initiates a storage of a measured pulse width upon a negative trailing edge of the output signal from the time-out circuit 76 and a simultaneous low output signal from the comparator Logical_PS and thus prepares the circuit for the next measurement.

Figure 8:
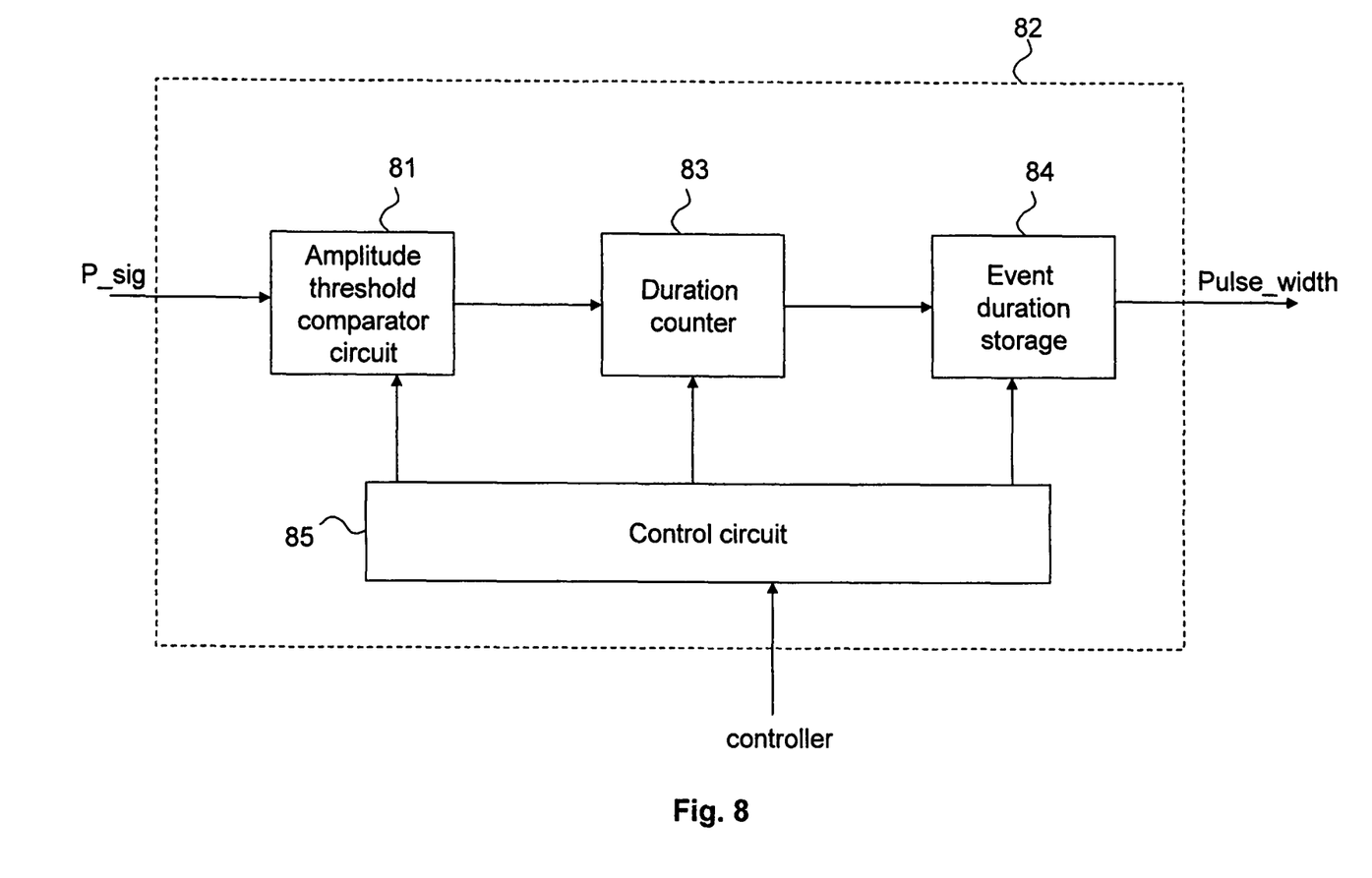
FIG. 8 is a block diagram of the functional components of another embodiment of the pulse width calculation block according to the present invention.

With reference now to FIG. 8, another embodiment of the pulse width calculation block will be shown. As mentioned above, the extracted signal P_sig, i.e. the rectified signal or the absolute value of the filtered signal, is supplied to the pulse width calculation block from the pre-processing circuits. The pulse width calculation block 82 comprises an amplitude threshold comparator circuit 81 adapted to cut out the part of the signal above a predetermined amplitude level. The amplitude level is programmable. A duration counter 83 is adapted to measure the duration of the resulting truncated signal to obtain a pulse width. The calculated pulse width is stored in a event duration storage 84. The measured duration Pulse_width can be stored, for example, in the memory means 31 for use in an optimization procedure and may also be supplied directly to the controller 27 for use in the optimization procedure. A control circuit 85 controls, under influence of the controller 27, the duration counter 83 and duration storage 84. The control circuit 85 resets the time duration counter 83 and initiates a storage of a measured pulse width and thus prepares the circuit for the next measurement.

Figure 9:
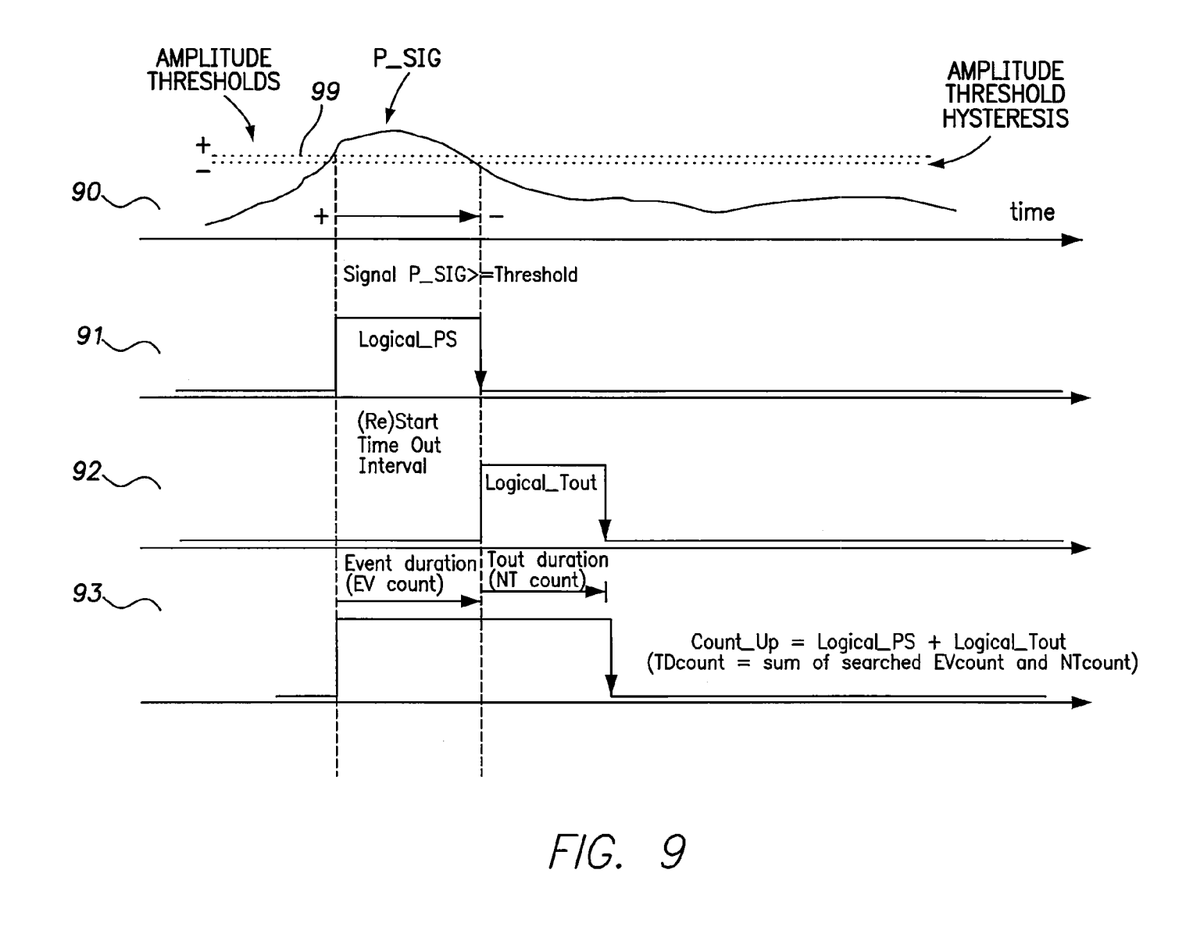
FIG. 9 shows a first example of signal waveforms in the signal processing circuit and the pulse width calculation block described with reference to FIG. 7 resulting from a sensed signal corresponding to a first heart sound.
Figure 10:
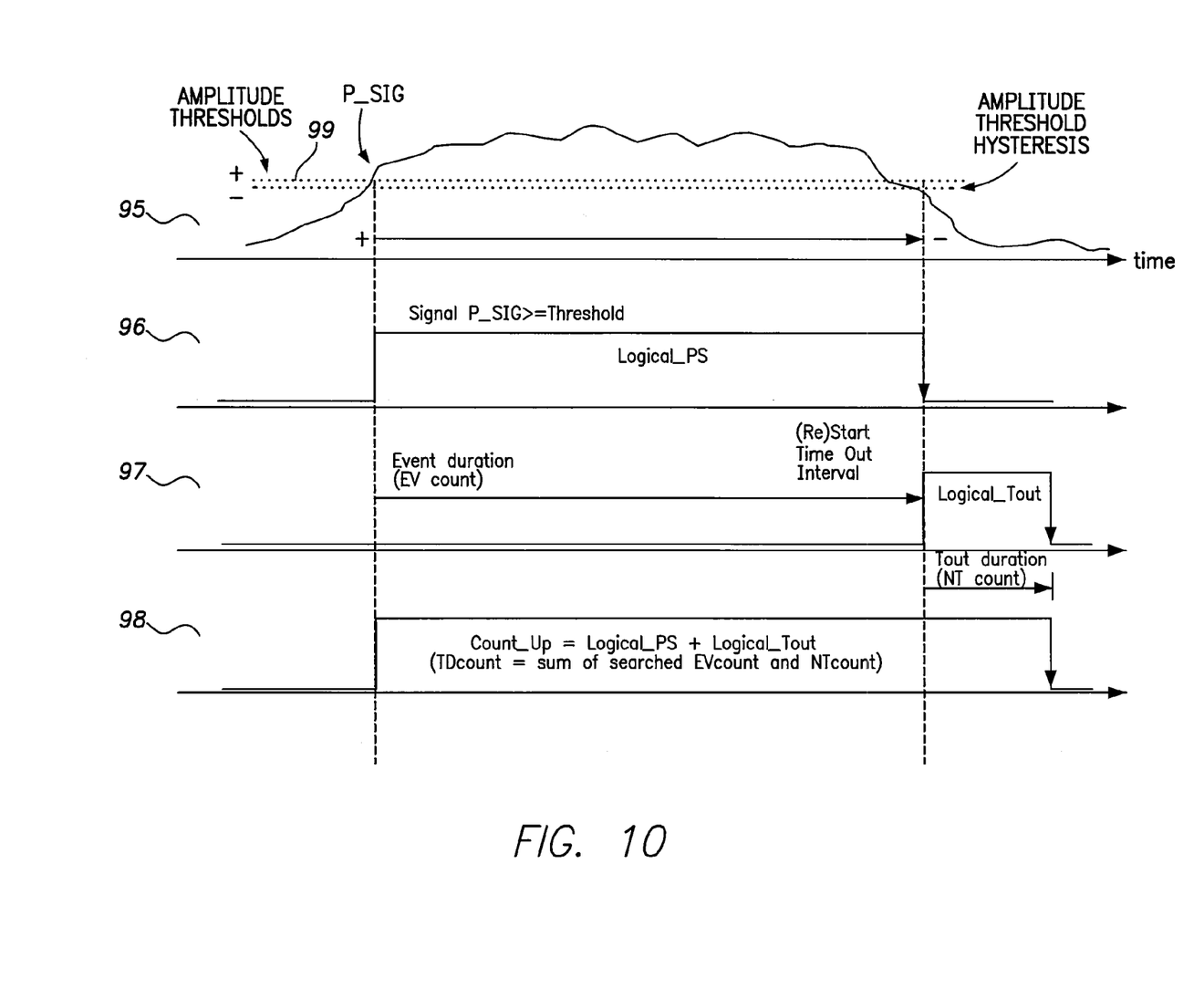
FIG. 10 shows a second example of signal waveforms in the signal processing circuit and the pulse width calculation block described with reference to FIG. 7 resulting from a sensed signal corresponding to a first heart sound.
Figure 11:
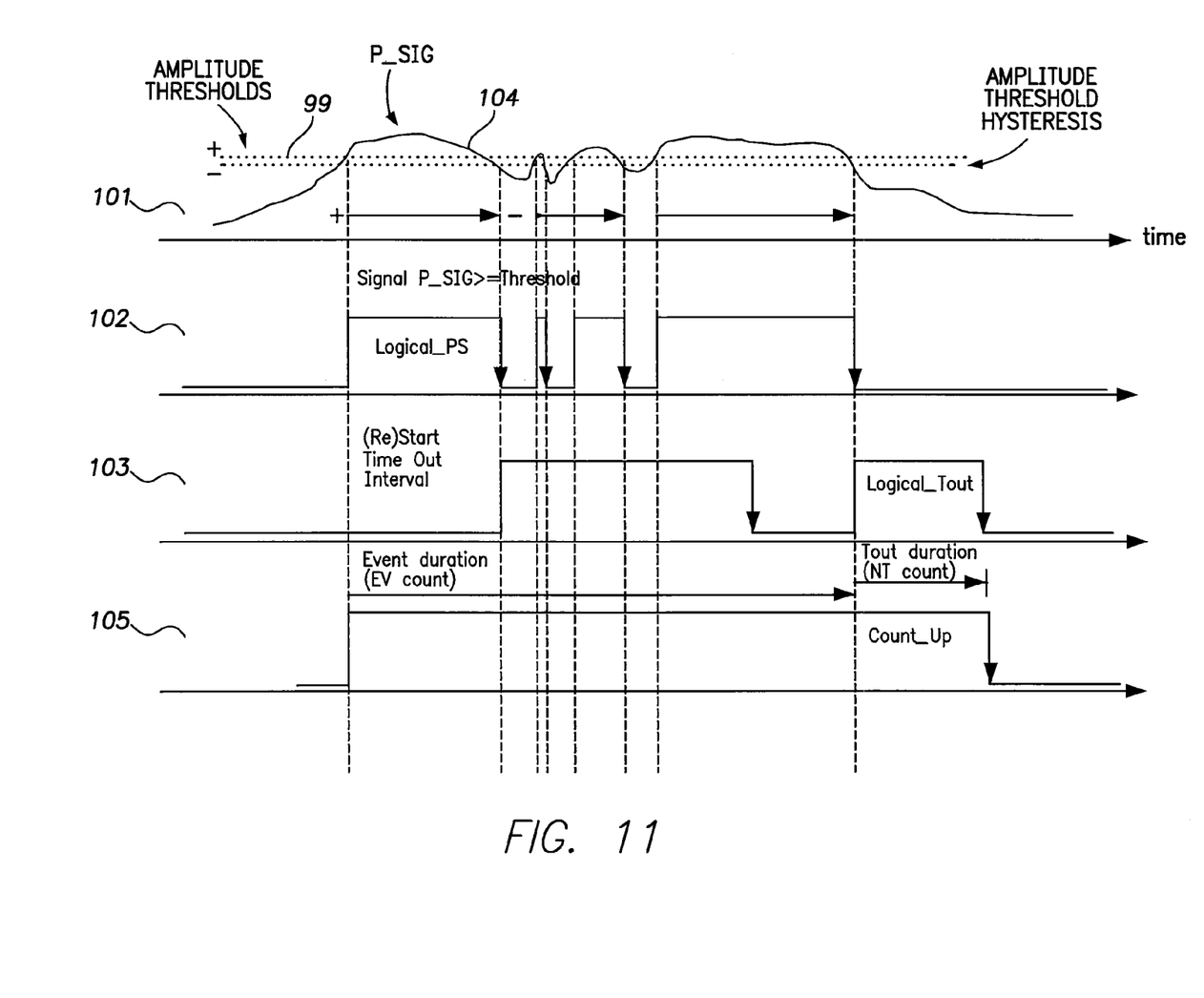
FIG. 11 shows a third example of signal waveforms in the signal processing circuit and the pulse width calculation block described with reference to FIG. 7 resulting from a sensed signal corresponding to a first heart sound.

Turning now to FIGS. 9-11, examples of signal waveforms in the signal processing circuit and the pulse width calculation block described with reference to FIG. 7 will be discussed. With reference to FIG. 9 an example with a signal of a short duration will be discussed. A signal P_sig is received from the pulse width calculation block 72 from the pre-processing circuits 30, 32, as indicated by the reference numeral 90. The comparator output signal Logical_PS is indicated by the reference numeral 91 and the time-out circuit output signal Logical_Tout is indicated by the reference numeral 92. In this case the amplitude of the signal is above the set amplitude thresholds 99 during the whole sensing session, i.e. the whole time window. The resulting output signal Count_up from the OR-circuit 71 is as indicated by the reference numeral 93.

Turning now to FIG. 10, an example with a signal of a long duration will be discussed. A signal P_sig is received from the pulse width calculation block 72 from the pre-processing circuits 30, 32, as indicated by the reference numeral 95. The comparator output signal Logical_PS is indicated by the reference numeral 96 and the time-out circuit output signal Logical_Tout is indicated by the reference numeral 97. In this case the amplitude of the signal is above the set amplitude thresholds 99 during the whole sensing session, i.e. the whole time window. The resulting output signal Count_up from the OR-circuit 71 is as indicated by the reference numeral 98.

Referring now to FIG. 11, an example with a signal of a long duration but with an amplitude that fluctuates about the thresholds 99 during the sensing session will be discussed. A signal P_sig is received from the pulse width calculation block 72 from the pre-processing circuits 30, 32, as indicated by the reference numeral 101. The reference numeral 102 indicates the Logical_PS, i.e. the output signal from the comparator 70, and, as can be seen, the signal will toggle between a logical 1 and logical 0 depending on the amplitude level of P_sig. As indicated by the reference numeral 103, which refers to the Logical_Tout signal, the time out interval is started when the Logical_PS signal becomes a logical 0 due to that the amplitude of P_sig falls below the amplitude thresholds the first time as indicated by 104. Thus, the Logical_Tout signal will bridge the periods of P_sig when the amplitude is below the amplitude thresholds and the OR-circuit 73 will supply a Count_up signal that reflects the correct pulse width, which is indicated by the reference numeral 105.

Although modifications and changes may be suggested by those skilled in the art, it is the intention of the inventors to embody within the patent warranted heron all changes and modifications as reasonably and properly come within the scope of their contribution to the art.

We claim as our invention:

1. An implantable medical device comprising:
   a pulse generator that emits cardiac stimulating pacing pulses including ventricular pacing pulses;
   an electrode lead connected to said pulse generator configured to deliver said ventricular pacing pulses to cardiac tissue in at least one ventricle of a heart of a patient;
   an acoustic sensor configured to sense acoustic energy from the patient and to emit an electrical signal indicative of heart sounds of the heart of the patient over a predetermined period of a cardiac cycle during successive cardiac cycles;
   a signal processor supplied with said electrical signal and configured to extract an extracted signal therefrom corresponding to the heart sound, known and designated as the first heart sound, and to calculate a pulse width of the extracted signal for each of a plurality of said successive cardiac cycles; and
   a controller supplied with the calculated pulse widths and configured to initiate an optimization procedure by controlling said pulse generator to iteratively control delivery of said ventricular pacing pulses based on the calculated pulse widths to said at least one ventricle, wherein the controller is configured to identify an interval selected from the group consisting of an RV interval and a VV interval that brings the respective pulse widths of said heart sound signals in said successive cardiac cycles to within a predetermined pulse width range or minimizes said pulse width.

2. An implantable medical device as claimed in claim 1 wherein said signal processor is configured to calculate each pulse width as an average value over a predetermined number of successive pulse widths of successive heart sound signals in said successive cardiac cycles.

3. An implantable medical device as claimed in claim 1 wherein said signal processor comprises:
   a bandpass filter that is configured to filter out frequency components of said electrical signals that are outside of a predetermined frequency range, to produce a filtered signal;
   a determining circuit that is configured to determine an absolute value of said filtered signal; and
   a pulse width calculation unit that is configured to calculate the pulse width of the filtered signal as said pulse width of said heart sound signal.

4. An implantable medical device as claimed in claim 3 wherein said pulse width calculating unit is configured to calculate the pulse width from a portion of the filtered signal that is above a predetermined amplitude threshold.

5. An implantable medical device as claimed in claim 1 wherein said signal processor is configured to extract said extracted signal from said electrical signal by selecting a portion of said electrical signal above a predetermined threshold, as a selected portion, and to calculate said pulse width based on said selected portion.

6. An implantable medical device as claimed in claim 1 comprising an activity level sensor configured to sense an activity level of the patient and to emit an activity signal dependent thereon, and wherein said controller is configured to determine whether said activity level of said activity signal is below a predetermined activity level, and to initiate said optimization procedure only when said activity level is below said predetermined activity level.

7. An implantable medical device as claimed in claim 1 comprising an activity level sensor configured to sense an activity level of the patient and to emit an activity signal corresponding thereto, and wherein said controller is configured to determine whether said activity level is below a predetermined first activity level or within an activity level range between a second activity level and a third activity level, said second activity level being equal to or higher than said first activity level, and when said activity level is below the predetermined first activity level, to initiate said optimization procedure to identify a first RV interval or a first VV interval that synchronizes closure of said mitral valve and tricuspid valve below said first activity level, and when said sensed activity level is within said activity level range, to initiate said optimization procedure to identify a second RV interval or a second VV interval that synchronizes closure of the mitral valve and the tricuspid valve in said activity level range.

8. An implantable medical device as claimed in claim 1 comprising a heart rate sensor that senses a heart rate of the patient, and wherein said controller is configured to determine whether said heart rate is within a predetermined heart rate interval and to initiate said optimization procedure when said heart rate is within said predetermined heart rate interval.

9. An implantable medical device as claimed in claim 1 comprising a sensing circuit that senses an AV interval of the patient, and wherein said controller is configured to determine whether the AV interval is within a predetermined AV interval range and to initiate said optimization procedure when said AV interval is within the predetermined AV interval range.

10. An implantable medical device as claimed in claim 1 comprising a position detecting sensor that detects a body position of the patient, and wherein said controller is configured to determine whether said patient is in at least one predetermined body position and to initiate said optimization procedure when said patient is in said at least one predetermined body position.

11. An implantable medical device as claimed in claim 1 wherein said acoustic sensor is adapted to be carried by a lead connected to said signal processor.

12. An implantable medical device as claimed in claim 1 comprising a housing containing said pulse generator, said signal processor, and said controller, and wherein said acoustic sensor is disposed within said housing.

13. An implantable medical device as claimed in claim 1 further comprising a lead that carries said acoustic sensor and is adapted to be connected to said signal processor, and wherein said lead is configured for placement of said acoustic sensor at a location selected from the group consisting of in the right ventricle of the heart, in the coronary vein of the heart, and in the right atrium of the heart.

14. An implantable medical device as claimed in claim 1 wherein said acoustic sensor is a sensor selected from the group consisting of accelerometers, pressure sensors, and microphones.

15. In an implantable medical device, a method for pacing a heart comprising the steps of:
   emitting cardiac stimulating pacing pulses and delivering said pacing pulses to cardiac tissue in at least one ventricle of a heart of a patient;
   sensing acoustic energy from the patient and emitting an electrical signal indicative of heart sounds of the heart of the patient over a predetermined period of a cardiac cycle during successive cardiac cycles;
   processing said electrical signal and to extract an extracted signal therefrom corresponding to the heart sound, known and designated as the first heart sound, and to calculate a pulse width of the extracted signal for each of a plurality of said successive cardiac cycles;

automatically electronically initiating an optimization procedure to iteratively control delivery of pulses to said at least one ventricle based on the calculated pulse width; and identifying an interval selected from the group consisting of an RV interval and a VV interval that brings the respective pulse widths of said heart sound signals in said successive cardiac cycles to within a predetermined pulse width range or minimizes said pulse width.

16. A method as claimed in claim 15 comprising automatically electronically calculating each pulse width as an average value over a predetermined number of successive pulse widths of successive heart sound signals in said successive cardiac cycles.

17. A method as claimed in claim 15 comprising processing said electrical signal by:

filtering out frequency components of said electrical signals that are outside of a predetermined frequency range, to produce a filtered signal; determining an absolute value of said filtered signal; and calculating the pulse width of the filtered signal as said pulse width of said heart sound signal.

18. A method as claimed in claim 17 comprising calculating the pulse width from a portion of the filtered signal that is above a predetermined amplitude threshold.

19. A method as claimed in claim 15 comprising extracting said extracted signal from said electrical signal by selecting a portion of said electrical signal above a predetermined threshold, as a selected portion, and calculating said pulse width based on said selected portion.

20. A method as claimed in claim 15 comprising sensing an activity level of the patient and emitting an activity signal dependent thereon, and determining whether said activity level of said activity signal is below a predetermined activity level, and initiating said optimization procedure only when said activity level is below said predetermined activity level.

21. A method as claimed in claim 15 comprising sensing an activity level of the patient and emitting an activity signal corresponding thereto, and determining whether said activity level is below a predetermined first activity level or within an activity level range between a second activity level and a third activity level, said second activity level being equal to or higher than said first activity level, and when said activity level is below the predetermined first activity level, initiating said optimization procedure to identify a first RV interval or a first VV interval that synchronizes closure of said mitral valve and tricuspid valve below said first activity level, and when said sensed activity level is within said activity level range, initiating said optimization procedure to identify a second RV interval or a second VV interval that synchronizes closure of the mitral valve and the tricuspid valve in said activity level range.

22. A method as claimed in claim 15 comprising sensing a heart rate of the patient, and determining whether said heart rate is within a predetermined heart rate interval and initiating said optimization procedure when said heart rate is within said predetermined heart rate interval.

23. A method as claimed in claim 15 comprising sensing an AV interval of the patient, and determining whether the AV interval is within a predetermined AV interval range and initiating said optimization procedure when said AV interval is within the predetermined AV interval range.

24. A method as claimed in claim 15 comprising detecting a body position of the patient, and determining whether said patient is in at least one predetermined body position and initiating said optimization procedure when said patient is in said at least one predetermined body position.

25. A method as claimed in claim 15 comprising emitting said cardiac pacing pulses to said at least one ventricle and processing said electrical signals in a housing configured for implantation in a subject, and mounted said acoustic sensor within said housing.

26. A method as claimed in claim 15 comprising implanting a lead carrying said acoustic sensor in a subject, and placing said acoustic sensor carried by said lead at a location selected from the group consisting of in the right ventricle of the heart, in the coronary vein of the heart, and in the right atrium of the heart.

27. A method as claimed in claim 15 comprising selecting said acoustic sensor from the group consisting of accelerometers, pressure sensors, and microphones.

* * * * *